United States Patent [19]

Böhner et al.

[11] 4,395,277
[45] Jul. 26, 1983

[54] [4-(5'-TRIFLUOROMETHYLPYRIDYL-2'-OXY)-PHENOXY]-PROPIONIC ACID ESTERS WITH α-HYDROXY OR α-MERCAPTO GAMMA-BUTYROLACTONE AND THEIR USE AS HERBICIDES

[75] Inventors: Beat Böhner, Binningen; Hermann Rempfler, Ettingen, both of Switzerland

[73] Assignee: Ciba-Geigy Corporation, Ardsley, N.Y.

[21] Appl. No.: 288,860

[22] Filed: Jul. 31, 1980

[30] Foreign Application Priority Data

Aug. 11, 1980 [CH] Switzerland ............... 6060/80

[51] Int. Cl.³ ............... A01N 43/40; C07D 413/12
[52] U.S. Cl. ............... 71/94; 546/283
[58] Field of Search ............... 546/283; 71/94

[56] References Cited

FOREIGN PATENT DOCUMENTS 2804074 8/1978 Fed. Rep. of Germany .

*Primary Examiner*—Henry R. Jiles
*Assistant Examiner*—Bernard Dentz
*Attorney, Agent, or Firm*—Frederick H. Rabin

[57] ABSTRACT

Novel α-[4-(5'-trifluoromethylpyridyl-2'-oxy)-phenoxy]-propionic acid -γ-butyrolactone esters and -thioesters of the formula

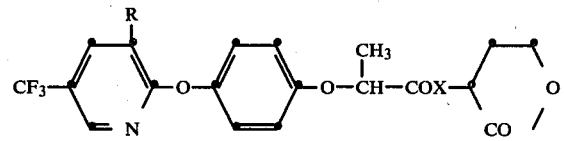

wherein R is hydrogen or chlorine, and X is oxygen or sulfur, which compounds have herbicidal activity. They are especially suitable for selectively combating gramineous weeds in cultivated crops. These compounds are produced by esterifing pyridyloxy-phenoxypropionic acid with α-bromo-γ-butyrolactone.

8 Claims, No Drawings

[4-(5'-TRIFLUOROMETHYLPYRIDYL-2'-OXY)-PHENOXY]-PROPIONIC ACID ESTERS WITH α-HYDROXY OR α-MERCAPTO GAMMA-BUTYROLACTONE AND THEIR USE AS HERBICIDES

The present invention relates to novel α-[4-(5'-trifluoromethylpyridyl-2'-oxy)-phenoxy]-propionic acid-γ-butyrolactone esters and -thioesters having herbicidal activity, to processes for producing them, and to compositions containing these esters as active ingredients, and also to the use thereof for combating undesirable plant growth.

The α-[4-(5'-trifluoromethylpyridyl-2'-oxy)-phenoxy]-propionic acid-γ-butyrolactone esters and -thioesters correspond to the formula I

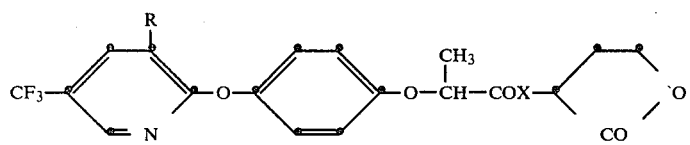

wherein R is hydrogen or chlorine, and X is oxygen or sulfur.

The following compounds are embraced by the formula:
α-[4-(5'-trifluoromethylpyridyl-2'-oxy)-phenoxy]-propionic acid-γ-butyrolactone ester,
α-[4-(3'-chloro-5'-trifluoromethylpyridyl-2'-oxy)-phenoxy]-propionic acid-γ-butyrolactone ester,
α-[4-(5'-trifluoromethylpyridyl-2'-oxy)-phenoxy]-propionic acid-γ-butyrolactone thioester, and
α-[4-(3'-chloro-5'-trifluoromethylpyridyl-2'-oxy)-phenoxy]-propionic acid-γ-butyrolactone thioester.

Phenoxy-phenoxy-alkanecarboxylic acid-γ-butyrolactone esters having herbicidal activity have been described in the German Offenlegungsschrift No. 2,804,074. The compounds of the present application are novel and surprisingly exhibit an excellent herbicidal activity which exceeds that of the esters of the German Offenlegungsschrift No. 2,804,074, and they moreover have interesting properties of selectivity with respect to individual cultivated plants, for example soyabean plants.

The novel α-[4-(5'-trifluoromethylpyridyl-2'-oxy)-phenoxy]-propionic acid-γ-butyrolactone esters and -thioesters of the formula I as well as the compositions containing them have, even when applied in small amounts, an excellent, selective-herbicidal action against weeds in various cultivated crops, particularly in dicotyledonous cultivated crops.

A preferred field of application is the combating of gramineous varieties of weeds in cultivated crops, for example in cotton, sugar-beet, soyabean and vegetable crops.

Although the novel active substances of the formula I are effective in both the pre-emergence and post-emergence process, the post-emergence application of the compounds as contact herbicides appears to deserve preferance; the pre-emergence form of application is nevertheless also of interest.

The novel active substances are preferably formulated for example as 25% wettable powders or as 20% emulsifiable concentrates and, diluted with water, applied to the crops after emergence of the plants.

The compounds of the present invention have negligible toxicity to warm-blooded animals, and the compounds can be handled without special precautionary measures. They are advantageously used in the field in amounts of 5 kg per hectare and less. They can be used in the pre-emergence process, but are preferably applied after emergence of the crops.

For broadening their activity spectrum or to obtain a desired synergistic or also antagonistic effect, the compounds of the invention can be used together with known herbicidal, pesticidal or fungicidal compounds. Suitable products for forming a combination are for example the preparations described in the "Pesticidal Manual" 6th Edition, published by the British Crop Protection Council, ISBN 0-901 436-44-5.

The novel active substances of the formula I are stable compounds which are soluble in customary organic solvents, such as alcohols, ethers, ketones, dimethylformamide, dimethyl sulfoxide, and so forth.

The compositions according to the invention are produced in a manner known per se by the intimate mixing and grinding of active substances of the general formula I with suitable carriers and/or distributing agents, optionally with the addition of antifoaming agents, wetting agents, dispersing agents and/or solvents, all inert to the active substances. The active substances can be obtained and used in the following forms:

solid preparations: dusts, scattering agents, granulates (coated granules, impregnated granules and homogeneous granules);

water-dispersible concentrates of active substance: wettable powders, pastes, emulsions and emulsion concentrates, and liquid preparations: solutions.

The concentration of active substance in the compositions according to the invention is 1 to 80 percent by weight, and when being applied the compositions can if necessary contain the active substance also at a low concentration, such as about 0.05 to 1 percent by weight.

The α-[4-(5'-trifluoromethylpyridyl-2'-oxy)-phenoxy]-propionic acid-γ-butyrolactone esters and -thioesters of the formula I can be produced, in a manner known per se, by reaction of α-[4-(5'-trifluoromethylpyridyl-2'-oxy)-phenoxy]-propionic acid or -thiopropionic acid, or of α-[4-(3'-chloro-5'-trifluoromethylpyridyl-2'-oxy)-phenoxy]-propionic acid or -thiopropionic acid, in each case of the formula II

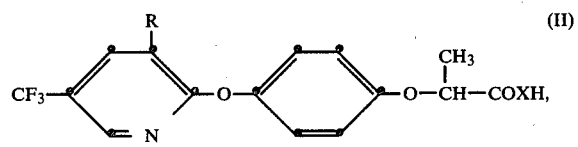

wherein R and X have the meanings given under the formula I, with α-bromo-γ-butyrolactone of the formula III

in an inert solvent and in the presence of an acid-binding agent.

The α-[4-(5'-trifluoromethylpyridyl-2'-phenoxy]-propionic acids and -thiopropionic acids required as starting products are known. The production thereof is described for example in the following publications: German Offenlegungsschriften Nos. 2,531,643 and 2,546,251, G.B. Patent Specification No. 1,507,643, U.S. Pat. No. 4,046,553 and Swiss Patent Application No. 14398/77. α-Bromo-γ-butyrolactone is obtainable commercially.

The following Example describes the production of a compound according to the invention. Temperature values are given in degrees Centigrade, and parts and percentages are by weight. In further Examples are described forms of preparation and also herbicidal test arrangements.

EXAMPLE 1

Production of α-[4-(3'-chloro-5'-trifluoromethylpyridyl-2'-oxy)-phenoxy]-propionic acid-γ-butyrolactone ester

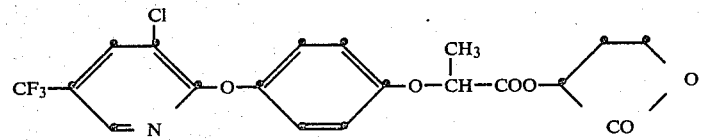

(a) 10.8 g (0.05 mol) of 2,3-dichloro-5-trifluoromethylpyridine are added dropwise to a suspension of 9.8 g (0.05 mol) of α-(4-hydroxyphenoxy)-propionic acid methyl ester and 8.3 g (0.06 mol) of potassium carbonate in 50 ml of ethyl methyl ketone, and the mixture is subsequently refluxed for 15 hours. The salts are filtered off and the filtrate is concentrated by evaporation. The oily residue is purified through silica gel with ethyl acetate/hexane 1:3 as the eluant. The yield is 16.9 g (90% of theory) of α-[4-(3'-chloro-5'-trifluoromethylpyridyl-2'-oxy)-phenoxy]-propionic acid methyl ester having a refractive index of $n_D^{30} = 1.5186$.

(b) 15 g (0.04 mol) of this methyl ester and 60 ml of 2 N sodium hydroxide solution are stirred at 70° for 2 hours. The mixture after cooling is acidified with concentrated hydrochloric acid and extracted with ether. The ether layer is dried over sodium sulfate and concentrated by evaporation. There are thus obtained 13.2 g (91% of theory) of α-[4-(3'-chloro-5'-trifluoromethylpyridyl-2'-oxy)-phenoxy]-propionic acid having a melting point of 104°–106°.

(c) 6.5 g (0.018 mol) of this propionic acid and 3 g (0.022 mol) of potassium carbonate are stirred in 40 ml of acetone at 40° for one hour. After the addition of 3.1 g (0.019 mol) of α-bromo-γ-butyrolactone, the suspension is stirred at 40° for a further 3 hours. The salts are then filtered off, the filtrate is concentrated by evaporation, and the residue is dissolved in carbon tetrachloride and treated with active charcoal. The yield after concentration by evaporation is 5.3 g (66% of theory) of α-[4-(3'-chloro-5'-trifluoromethylpyridyl-2'-oxy)-phenoxy]-propionic acid-γ-butyrolactone ester having a refractive index of $n_D^{30} = 1.5195$.

The following compounds are produced in an analogous manner:

α-[4-(5'-trifluoromethylpyridyl-2'-oxy)-phenoxy]-propionic acid-γ-butyrolactone ester, $n_D^{30} = 1.5127$, α-[4-(5'-trifluoromethylpyridyl-2'-oxy)-phenoxy]-propionic acid-γ-butyrolactone thioester, and α-[4-(3'-chloro-5'-trifluoromethylpyridyl-2'-oxy)-phenoxy]-propionic acid-γ-butyrolactone thioester.

EXAMPLE 2

Production of ready-for-use preparations

Emulsion concentrate

The following constituents are mixed together to produce a 25% emulsion concentrate:

25 parts of α-[4-(5'-trifluoromethylpyridyl-2'-oxy)-phenoxy]-propionic acid-γ-butyrolactone ester, 5 parts of a mixture of nonylphenolpolyoxyethylene and calcium dodecylbenzene sulfonate, 15 parts of cyclohexanone and 55 parts of xylene.

This concentrate can be diluted with water to give emulsions of suitable concentration, for example 0.1 to about 10%. Emulsions of this type are suitable for combating weeds in crops of cultivated crops.

Granulate

The following substances are used to produce a 15% granulate:

5 parts of α-[4-(5'-trifluoromethylpyridyl-2'-oxy)-phenoxy]-propionic acid-γ-butyrolactone thioester, 0.25 part of epoxidised vegetable oil,
0.25 part of cetyl polyglycol ether,
3.50 parts of polyethylene glycol and
91 parts of kaolin (particle size 0.3–0.8 mm).

The active substance is mixed with the vegetable oil and dissolved in 6 parts of acetone, and polyethylene glycol and cetyl polyglycol ether are then added. The solution thus obtained is sprayed onto kaolin, and the acetone is subsequently evaporated off in vacuo.

Wettable powders

The following constituents are used to produce (a) a 70% wettable powder and (b) a 10% wettable powder:

(a)

70 parts of α-[4-(3'-chloro-5'-trifluoromethylpyridyl-2'-oxy)-phenoxy]-propionic acid-γ-butyrolactone ester,
5 parts of sodium dibutyl-naphthalene sulfonate,
3 parts of naphthalenesulfonic acid/phenolsulfonic acid/formaldehyde condensate (3:2:1),
10 parts of kaolin,
12 parts of chalk powder;

(b)

10 parts of the above active substance, 3 parts of a mixture of the sodium salts of saturated fatty alcohol sulfonates,
5 parts of a naphthalenesulfonic acid/formaldehyde condensate and
82 parts of kaolin.

The given active substance is absorbed onto the appropriate carriers (kaolin and chalk), and the material is subsequently mixed and ground with the remaining constituents. Wettable powders having excellent wetting and suspension properties are obtained. It is possible to obtain from wettable powders of this type, by dilution with water, suspensions containing 0.1 to 8% of active substance, these suspensions being suitable for combating weeds in crops of cultivated plants.

Paste

The following substances are used to produce a 45% paste:
45 parts of α-[4-(3'-chloro-5'-trifluoromethylpyridyl-2'-oxy)-phenoxy]-propionic acid-γ-butyrolactone thioester,
5 parts of sodium aluminium silicate,
14 parts of cetyl polyglycol ether with 8 mols of ethylene oxide,
1 part of oleyl polyglycol ether with 5 mols of ethylene oxide,
2 parts of spindle oil,
10 parts of polyethylene glycol, and
23 parts of water.

The active substance is intimately mixed and ground with the additives in devices suitable for the purpose. There is obtained a paste from which suspensions of the concentration desired can be prepared by dilution with water.

Suspension concentrate

The following substances are used to produce a 45% suspension concentrate
45 parts of α-[4-(5'-trifluoromethylpyridyl-2'-oxy)-phenoxy]-propionic acid-γ-butyrolactone ester,
5 parts of ethylene glycol,
3 parts of octylphenoxypolyethylene glycol with 9-10 mols of ethylene oxide per mol of octylphenol,
3 parts of a mixture of aromatic sulfonic acids condensed with formaldehyde as ammonium salt,
1 part of silicone oil in the form of a 75% emulsion,
0.1 part of a mixture of 1-(3-chloroallyl)-3,5,7-triazoazonium-adamantane chloride with sodium carbamate, chloride value at least 11.5%,
0.2 part of a bipolymeric thickener having a maximum of 100 nuclei per gram, and
42.7 parts of water.

The active substance is mixed and ground with the additives in devices suitable for the purpose. There is obtained a paste from which can be produced, by dilution with water, suspensions of any concentration required.

EXAMPLE 3

The herbicidal activity is demonstrated by the following tests:

Herbicidal activity with application of the active substances after emergence of the plants (post-emergence)

Various cultivated plants and weeds are grown from seed in pots in a greenhouse until they have reached the 4- to 6-leaf stage. The plants are then sprayed with the aqueous active-substance emulsions (obtained from a 20% emulsifiable concentrate) using varying dosages. The treated plants are subsequently kept under optimum conditions of light, watering, temperature (22°–25° with 50–70% relative humidity). An assessment of the test is made 15 days after the treatment.

The condition of the plants is assessed on the basis of the following scale of ratings:

| 9 | plant has flourished as in the case of the untreated control plant, |
|---|---|
| 8–6 | slight damage, plant can recover, |
| 5–4 | moderate lasting damage, |
| 3–2 | severe damage, plant stunted, |
| 1 | plant has died off. |

The results are summarised below:

| Compound No. | 1 | | | |
|---|---|---|---|---|
| Amount applied kg/hectare | 1 | 0.5 | 0.25 | 0.125 |
| Plant | | | | |
| barley | 1 | 2 | 6 | 8 |
| wheat | 1 | 2 | 8 | 9 |
| soyabean | 9 | 9 | 9 | 9 |
| cotton | 9 | 9 | 9 | 9 |
| sugar-beet | 9 | 9 | 9 | 9 |
| Avena fatua | 1 | 1 | 5 | 7 |
| Alopecurus myosuroides | 1 | 2 | 2 | 4 |
| Digitaria sanguinalis | 1 | 1 | 1 | 2 |
| Echinochloa crus galli | 1 | 1 | 1 | 2 |
| Sorghum halepense | 1 | 1 | 1 | 2 |
| Rottboellia exaltata | 1 | 1 | 2 | 3 |

Herbicidal action on application of the active substances before emergence of the plants (pre-emergence)

Plant seeds are sown in pots in a greenhouse, and shortly afterwards the surface of the soil is treated with an aqueous active-substance emulsion or -suspension. The pots are then kept, with regular watering, at a temperature of 22°–25° with 50–70% relative humidity, until the test is terminated after 3 weeks. The condition of the plants is assessed according to the scale of ratings given in the foregoing. The results are summarised below:

| Compound No. | 1 | | |
|---|---|---|---|
| Amount applied in kg/hectare | 1 | 0.5 | 0.25 |
| Plant | | | |
| barley | 7 | 8 | 9 |
| wheat | 2 | 4 | 6 |
| maize | 3 | 6 | 8 |
| soyabean | 9 | 9 | 9 |
| cotton | 9 | 9 | 9 |
| sugar-beet | 9 | 9 | 9 |
| Avena fatua | 2 | 3 | 7 |
| Bromus tectorum | 1 | 2 | 4 |
| Alopecurus myosuroides | 1 | 1 | 3 |
| Digitaris sanguinalis | 1 | 1 | 1 |
| Achinochloa crus galli | 1 | 1 | 2 |
| Sorghum halepense | 1 | 1 | 1 |
| Rottboellia exaltata | 1 | 2 | 2 |

The compounds of the formula I control gramineous weeds in dicotyledonous crops such as soyabean, cotton and sugar-beet, but also in cereals and maize, both in the pre-emergence and post-emergence process, in small applied amounts of less than one kilogram of active substance per hectare.

What is claimed is:

1. α-[4-(5'-Trifluoromethylpyridyl-2'-oxy)-phenoxy]-propionic acid-γ-butyrolactone ester and -thioester of the formula I

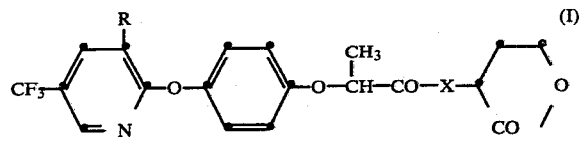

wherein R is hydrogen or chlorine, and X is oxygen or sulfur.

2. A compound of the formula I, claim 1, wherein X is oxygen.

3. α-[4-(5'-Trifluoromethylpyridyl-2'-oxy)-phenoxy]-propionic acid-γ-butyrolactone ester according to claim 2.

4. α-[4-(3'-Chloro-5'-trifluoromethylpyridyl-2'-oxy)-phenoxy]-propionic acid-γ-butyrolactone ester according to claim 2.

5. A herbicidal composition which contains a herbicidally effective amount of an α-[4-(5'-trifluoromethylpyridyl-2'-oxy)-phenoxy]-propionic acid-γ-butyrolactone ester or -thioester of the formula I, claim 1, as active ingredient, together with inert additives.

6. A method for selectively combating undesirable plant growth, which method comprises applying thereto or to the locus thereof a herbicidally effective amount of an α-[4-(5'-trifluoromethylpyridyl-2'-oxy)-phenoxy]-propionic acid-γ-butyrolactone ester of the formula I, claim 1.

7. A method for selectively combating gramineous weeds in dicotyledonous cultivated crops as well as in cereals and maize, which method comprises applying thereto or to the locus thereof a herbicidally effective amount of an α-[4-(5'-trifluoromethylpyridyl-2'-oxy)-phenoxy]-propionic acid-γ-butyrolactone ester of the formula I, claim 1.

8. A method for selectively combating gramineous weeds in cultivated crops of soyabean, which method comprises applying thereto or to the locus thereof a herbicidally effective amount of an α-[4-(5'-trifluoromethylpyridyl-2'-oxy)-phenoxy]-propionic acid-γ-butyrolactone ester of the formula I, claim 1.

* * * * *

UNITED STATES PATENT AND TRADEMARK OFFICE
CERTIFICATE OF CORRECTION

PATENT NO. : 4,395,277
DATED : July 26, 1983
INVENTOR(S) : Beat Böhner, et al

It is certified that error appears in the above-identified patent and that said Letters Patent are hereby corrected as shown below:

Cover page No. [22] Filing date reads Jul. 31, 1980.

Should read: -- Jul. 31, 1981 --

Signed and Sealed this

Fourth Day of October 1983

[SEAL]

Attest:

GERALD J. MOSSINGHOFF

Attesting Officer

Commissioner of Patents and Trademarks